United States Patent [19]

Khalil

[11] 4,240,441
[45] Dec. 23, 1980

[54] CAROTID THERMODILUTION CATHETER

[75] Inventor: Hassan H. Khalil, Alexandria, Egypt

[73] Assignee: The United States of America as represented by the Secretary of the Navy, Washington, D.C.

[21] Appl. No.: 950,196

[22] Filed: Oct. 10, 1978

[51] Int. Cl.³ ............................................. A61B 5/02
[52] U.S. Cl. .............................. 128/692; 128/700
[58] Field of Search ............... 128/670, 692, 713, 642, 128/700; 73/204

[56] References Cited

U.S. PATENT DOCUMENTS

| | | | |
|---|---|---|---|
| 3,075,155 | 1/1963 | Richards | 128/692 |
| 3,359,974 | 12/1967 | Khalil | 128/713 |
| 3,438,253 | 4/1969 | Kuether et al. | 73/244 |
| 3,478,588 | 11/1969 | Richardson | 73/362 |
| 3,595,079 | 7/1971 | Grahn | 73/204 |
| 3,623,364 | 11/1971 | Withrow | 73/204 |
| 3,722,505 | 3/1973 | Kolin | 128/692 |
| 3,734,083 | 5/1973 | Kolin | 128/692 |
| 3,789,831 | 2/1974 | Kopaniky et al. | 128/692 |
| 3,798,967 | 3/1974 | Gieles et al. | 73/204 |
| 3,995,623 | 12/1976 | Blake et al. | 128/642 |

OTHER PUBLICATIONS

*The Lancet*, Jun. 22, 1963, p. 1352.
*Journ. of Applied Physiol.*, vol. 21, 1966, p. 1131.
*World Conf. on Schistosomiasis Symposium*, Oct. 1975, paper by Khalil, H. H., pp. 1–20.
*Circulation Research*, vol. X, Mar. 1962, Hosie, K. F.
*American Heart Journ.*, vol. 83, No. 3, Mar. 1972, p. 306.

*Primary Examiner*—Kyle L. Howell
*Attorney, Agent, or Firm*—R. S. Sciascia; W. Thom Skeer; Timothy R. Schulte

[57] ABSTRACT

A thermodilution catheter having a proximal high frequency heating coil of fine wires, heat measuring thermocouples, and a distal resistance thermometer, all wound externally on a catheter for measuring arterial blood flow. The device also incorporates electrodes for electrocardiogram tracing.

8 Claims, 6 Drawing Figures

CAROTID THERMODILUTION CATHETER

BACKGROUND OF THE INVENTION

1. Field of the Invention

The invention pertains to the field of biomedical instrumentation. By way of further explanation, this invention pertains to the electronic instrumentation of the cardiovascular condition of a living organism. In still greater particularity the invention provides simultaneous indications of a plurality of cardiovascular conditions. This invention is further characterized by its use of thermodilution techniques to provide an indication of the quantity of blood flow in the cardiovascular system. Additionally this invention can provide an electrocardiogram tracing.

2. Description of the Prior Art

Thermodilution is an application of the calorimetric principle that, in a mixture of fluids at different temperatures, the heat lost by one fluid equals heat gained by the other. For each fluid, the mathematical product of the temperature change, specific heat and mass is equal.

A recognized method for the study of blood circulation involves producing a temperature change in the blood at one point in the blood flow and measuring the temperature change at a second downstream point. Assuming that the measurement of temperature change occurs at a point downstream of the heat source and that the blood's heat content is uniform the measured change will reflect the amount of blood passing through the blood vessel.

In thermodilution studies heat is either removed from or added to the blood stream. One technique involves the injection of a slightly cooler saline solution into the blood. It was introduced by Gegler in 1953 and involved the injection of cold blood or Ringer's solution and measurement of temperature in the pulmonary artery or aorta with thermocouples. The resulting temperature time curve resembled the previously used dye dilution methods of measuring cardiac output. However, this method requires an accurate measurement of the mass and temperature of each injection.

Methods of introducing heat to the blood flow itself have been developed. For example, in U.S. Pat. No. 3,438,253 issued to Fredric W. Kuether et al. on Apr. 15, 1969, a catheter with a heating coil of platinum ribbon, whose resistance changes with temperature, is described. By measuring the energy required to maintain the coil at a constant, elevated temperature, the velocity of blood flow may be determined. While satisfactory for its intended purpose of measuring velocity and direction of blood flow, this device uses continuous heating which could raise the overall temperature of the blood thus reducing accuracy. Furthermore, it is required to measure the cross sectional area of the vessel, which changes during each systole and diastole, and multiply the "velocity" by the cross section of the vessel to obtain volume flow. The velocity of fluid inside the vessels follows a parabolic function (Ruch & Fulten, Medical Physiology & Biphysics p. 248) and therefore the velocity obtained will depend on the position of the catheter inside the vessel and will change with any movement of the catheter to or from the center of the vessel.

In some devices, thermistors, or thermally sensitive resistors composed of an oxidic semiconductive material whose resistance varies with temperature, are employed as temperature measuring devices. A Wheatstone Bridge is used to measure resistance change in the sensing element. The sensing element is the resistance thermometer which is used as one arm of the Wheatstone Bridge. If the other three resistance arm values are known, and the bridge is balanced then no current passes through the galvanometer and the fourth resistance is easily calculated. Once the resistance value of the thermally sensitive resistor is known then the actual temperature is calculated.

Another heating method involves the introduction of heat at one point in the blood flow and the measurement of blood temperature at a downstream point. A device utilizing this method is shown in U.S. Pat. No. 3,359,974 issued to Hassan H. Khalil on Dec 26, 1967. This device uses a standard bilumen or trilumen cardiac catheter tube, about 3 mm dia., with fine lead wires connected to a heater winding, and a distal temperature transducer to measure the temperature change.

The heater winding is 12 to 15 cm of six fine enamel constantan wires, 0.04 mm dia. wound in parallel and soldered to the flattened tip of a lead wire as it emerges from a lumen of the catheter. The coil is heated with high frequency (350 Khz) current in order not to excite the myocardium. The temperature transducer is a fine nickel or platinum resistance thermometer in the form of a bifilar winding over the distal 16 cm of the catheter. The windings are covered with a thin layer of flexible varnish. The temperature transducer is connected to a three-lead thermometer bridge, a D.C. amplifier and recorder.

The catheter is designed so that the heating coil will be in the right atrium and superior vena cava and the temperature transducer will lie in the pulmonary artery. While satisfactory for its intended purposes, long areas of winding are necessary to eliminate errors introduced through incomplete blood mixing and laminar flow. In addition, direct readout is not available with this apparatus and it is therefore necessary to calculate the blood flow from observed data. Also, this device does not provide for electrocardiogram tracing.

SUMMARY OF THE INVENTION

The invention is a miniature thermodilution catheter for multiple measurements of Internal Carotid Blood flow and other regional blood flows in other accessible arteries. This catheter is inserted in the same direction as the blood flow when introduced through a carotid puncture and against the blood stream until it reaches the carotid artery when introduced through the femoral artery. The upstream high frequency heating coil is proximally located at the base of the catheter and the downstream platinum resistance thermometer is distally located at the tip of the catheter.

Fine lead wires are wound on the outside of the catheter and connected at solder points to the heating coil, which consists of six constantan wires bifilarly wound onto the catheter. The downstream resistance thermometer is also bifilarly wound.

A thermocouple measures temperature rise in the heating coil and is connected in series with a reference thermocouple, located proximally of the heating coil, to measure the local temperature rise at the heating coil. In addition, electrodes may be included on the long catheter introduced through the femoral artery so that an electrocardiogram tracting may be made.

DESCRIPTION OF THE PREFERRED EMBODIMENT

Figure 1:
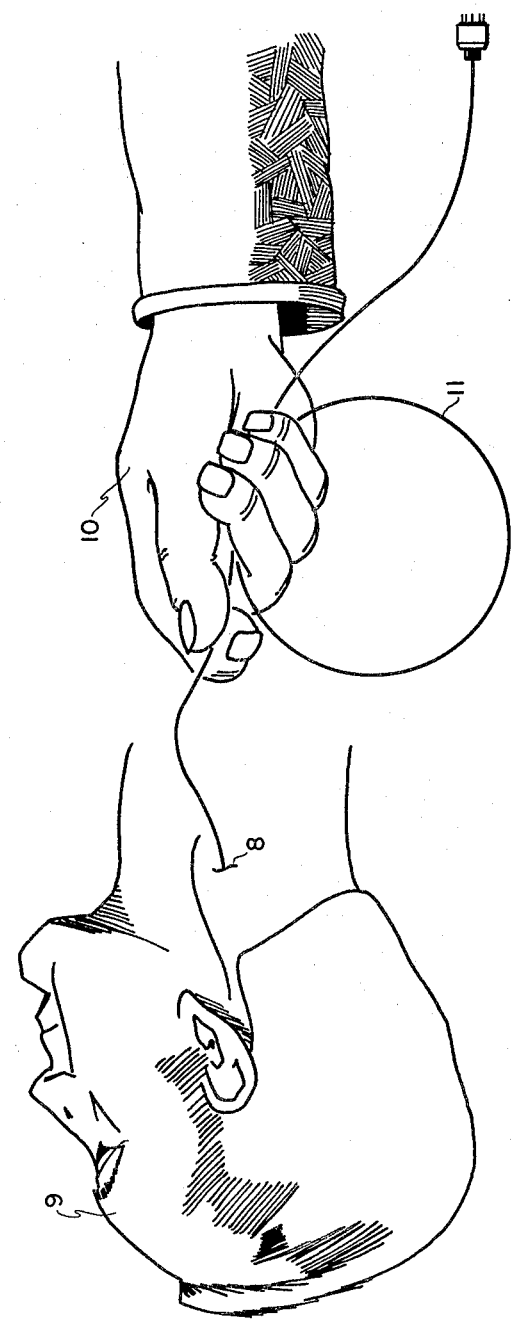
FIG. 1 is a perspective view showing the invention being used to measure Internal Carotid blood flow.

Referring to FIG. 1 a catheter 11 is inserted into living organism 9 by operator 10 through a puncture 8 in the internal carotid artery or the femoral artery.

Figure 2:
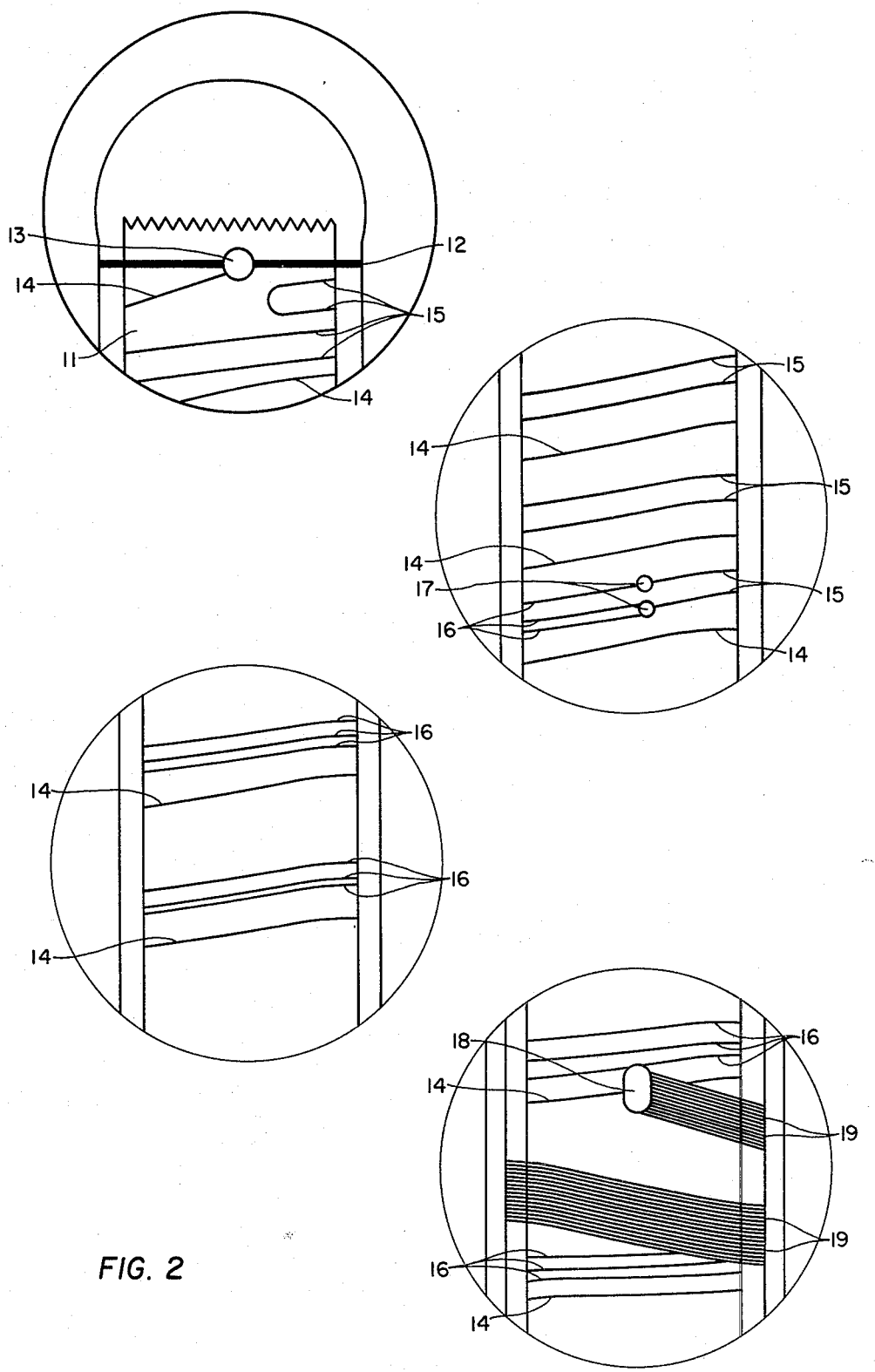
FIG. 2 is a segmented view of the distal or tip portion of the catheter.

Referring to FIG. 2, the invention is built upon catheter 11 which is preferably 0.7–0.8 mm in diameter for the measurement of arterial blood flow. Electric conductor or platinum wire electrode 12 for electrocardiogram tracing, is mounted at the tip of catheter 11. Lead wire 14 is electrically connected to platinum wire electrode 12 at solder point 13. Platinum resistance thermometer 15 is bifilarly wound onto catheter 11 starting at a point just proximal to platinum wire electrode 12. Platinum resistance thermometer 15 continues bifilarly wound on catheter 11 to solder points 17. From solder points 17 three lead wires 16 emanate. Heating coil 19, consisting of two bifilarly wound strands of 6 fine constantan wires, begins at solder point 18 and continues proximally down catheter 11.

Figure 3:
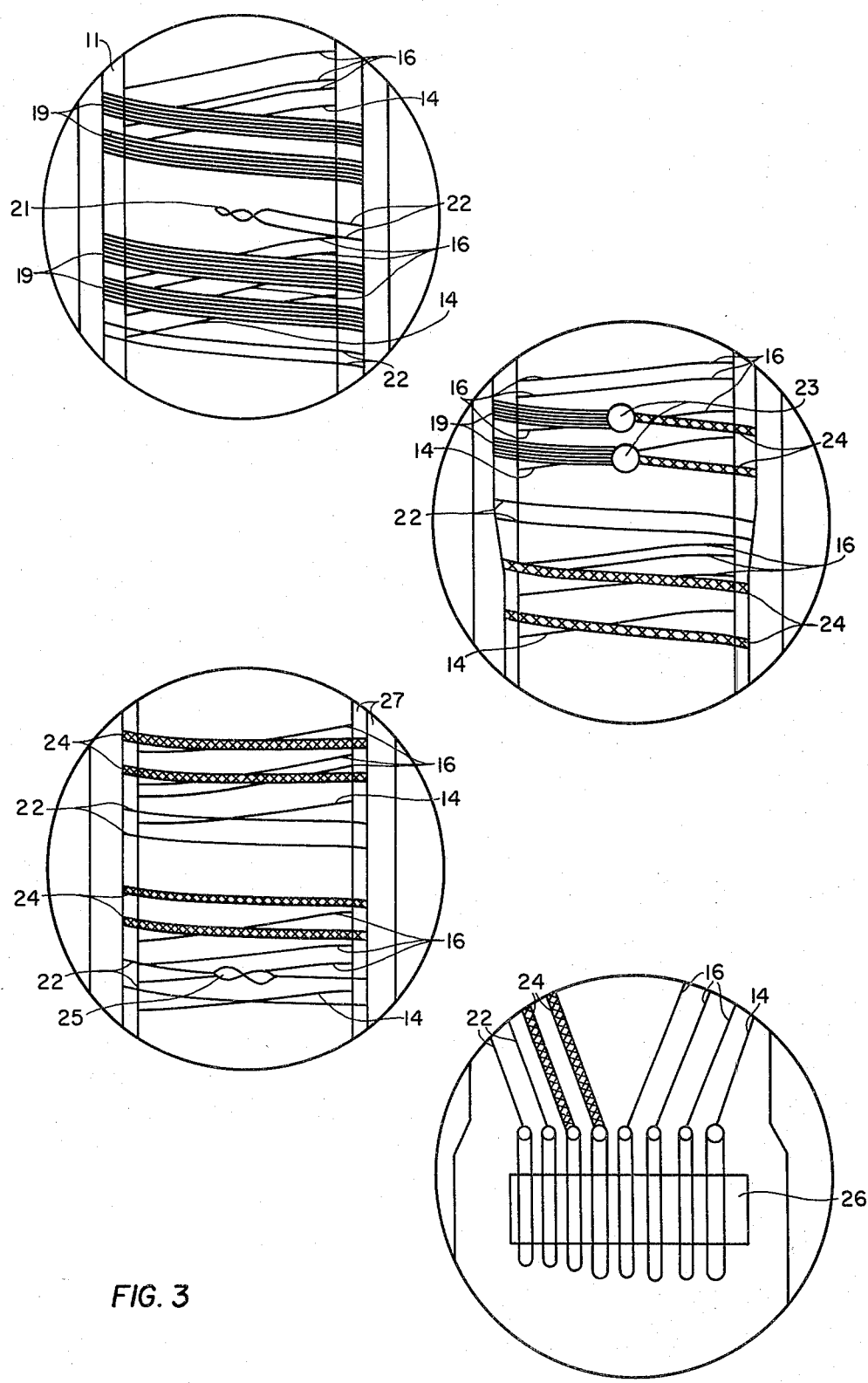
FIG. 3 is a segmented view of the portion of the catheter proximal to the heating coil at the tip and the base portion showing the connections to the plug.

Referring to FIG. 3, copper constantan thermocouple 21 is mounted between heating coil windings 19. Lead wires 22 connect copper constantan thermocouple 21 in series with reference copper constantan thermocouple 25. These thermocouples are used as temperature transducers to provide a convenient measure of the local temperature rise at heating coil 19. Lead wires 22 continue proximally on catheter 11 to plug 26. Heating coil 19 terminates in solder points 23 from which two lead wires 24 emanate. Lead wires 24 terminate at plug 26. Lead wires 16 from platinum resistance thermometer 15 (see FIG. 2) also terminate at plug 26. Similarly lead wire 14, from platinum electrode 12 (see FIG. 2) terminates at plug 26.

Plug 26 connects the catheter assembly to the electronics necessary to obtain the thermodilution measurements. Catheter 11 which is a flexible, woven body along with the rest of the above described apparatus is covered with inert plastic coating 27 which is applied in 3 layers after winding the wires. The multiple layers ensure perfect electric insulation. The plastic is diluted with ethyl acetate to make each layer as thin as possible. A layer is also placed on the inside of catheter 11. Silicone rubber may be used as inert plastic coating 27.

Figure 4:
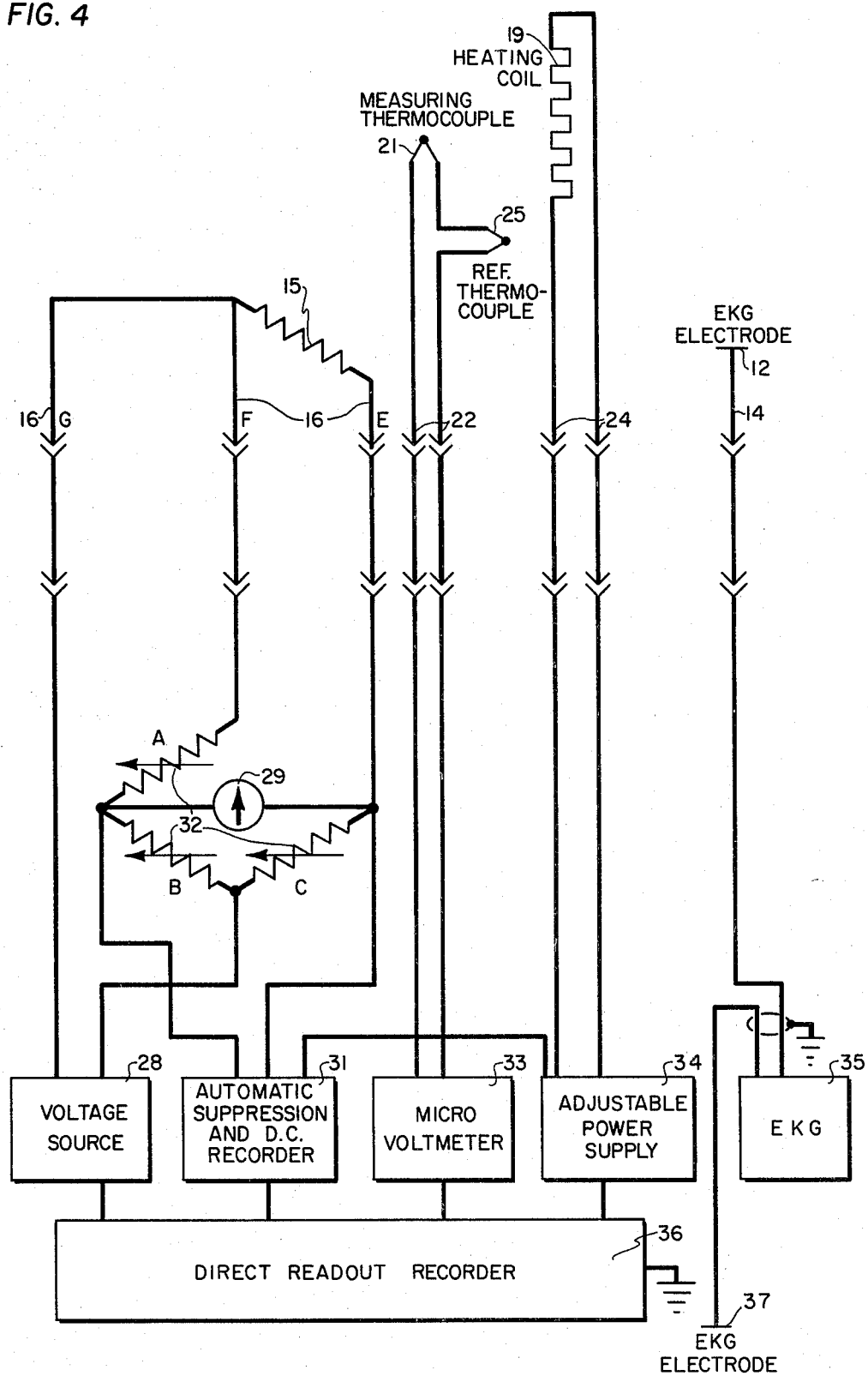
FIG. 4 is a schematic representing the electronic aspects of the invention.

Referring now to FIG. 4, platinum resistance thermometer 15 is one arm of a Wheatstone Bridge. Standard voltage source 28, which may be, for example, a 1.35 volt mercury battery, galvanometer 29, automatic balance and D.C. recorder 31, and three variable resistors 32 A-C comprise the bridge. Two leads 16E and 16F are used to connect thermometer 15 to variable resistors 32. Thermometer 15 thus forms one arm of the bridge. Lead 16G is connected to standard voltage source 28 to energize the bridge. Temperature changes down to 0.001° C. can easily be detected using this configuration.

Thermocouples 21 and 25, located on the catheter in the heating coil region are connected to microvoltmeter 33 by lead wires. These temperature transducers permit accurate measurement of the local temperature rise.

Heating coil 19 is connected to adjustable power supply 34 by lead wires 24. Power supply 34 is adjustable so that the rate of heating of the coil may be accurately determined prior to applying power to the catheter. Electrode 12 is connected to electrocardiograph 35 by lead 14. Electrode 37 may be mounted either on catheter 11 or placed directly on living organism 9. Finally electronic components 28, 31, 33, and 34 are connected to direct readout recorder 36.

MODE OF OPERATION

The Internal Carotid Catheter is similar in design and structure to the Khalil Cardiac Thermodilution Catheter as described in U.S. Pat. No. 3,359,974 issued to Hassan H. Khalil on Dec. 26, 1967. However, the internal carotid catheter is different in that it is much smaller, 0.7–0.8 millimeters O.D., at heating coil 19 and 0.5 millimeters, O.D. at platinum resistance thermometer 15. In addition, with the present invention the blood flow measurements are independent of blood mixing and laminar flow. This is because the ratio between the surface area of heating coil 19 and the volume flow is much higher than that in the cardiac catheter.

Figure 5:
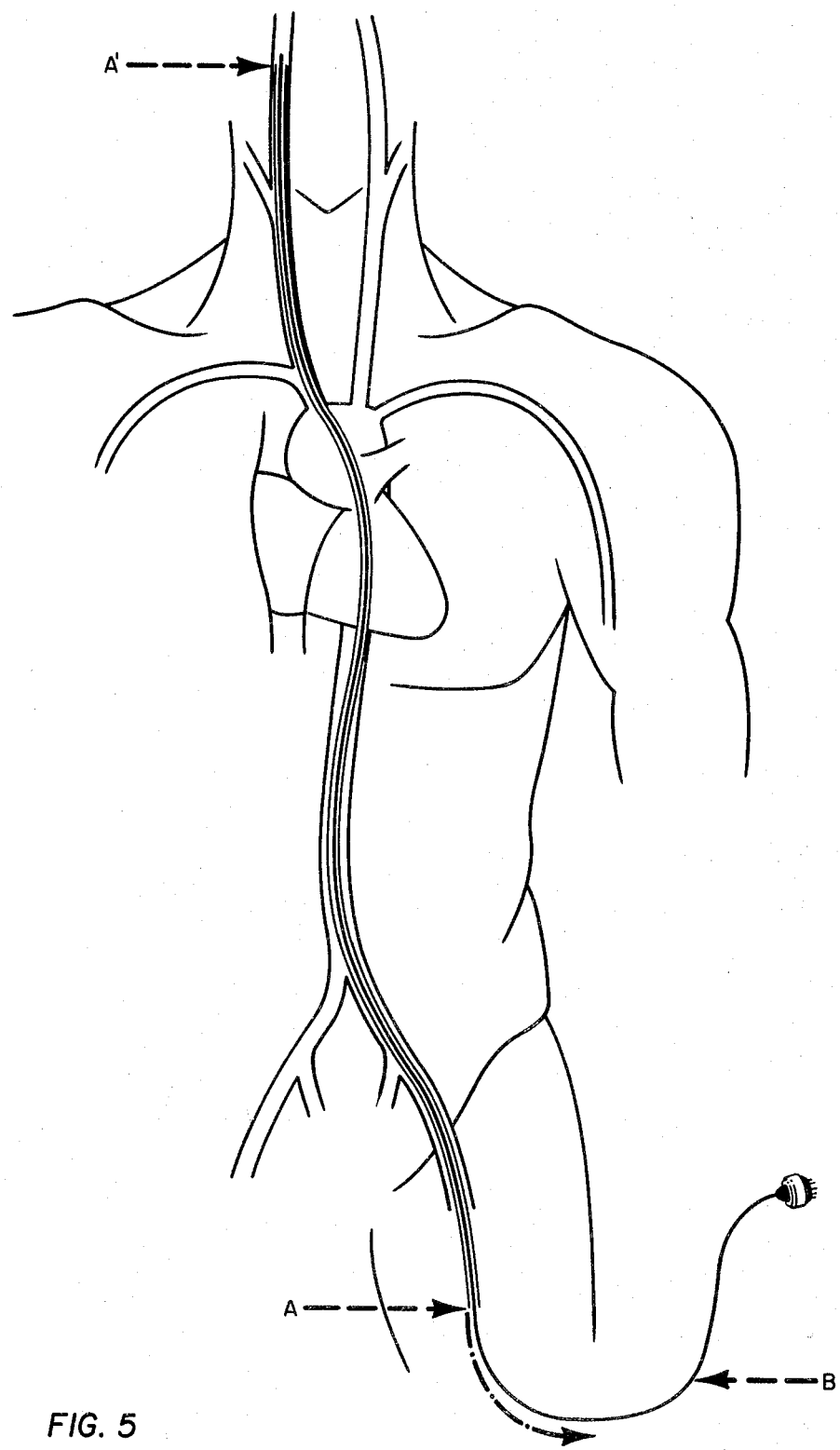
FIG. 5 shows the insertion of the catheter into the femoral artery.
Figure 6:
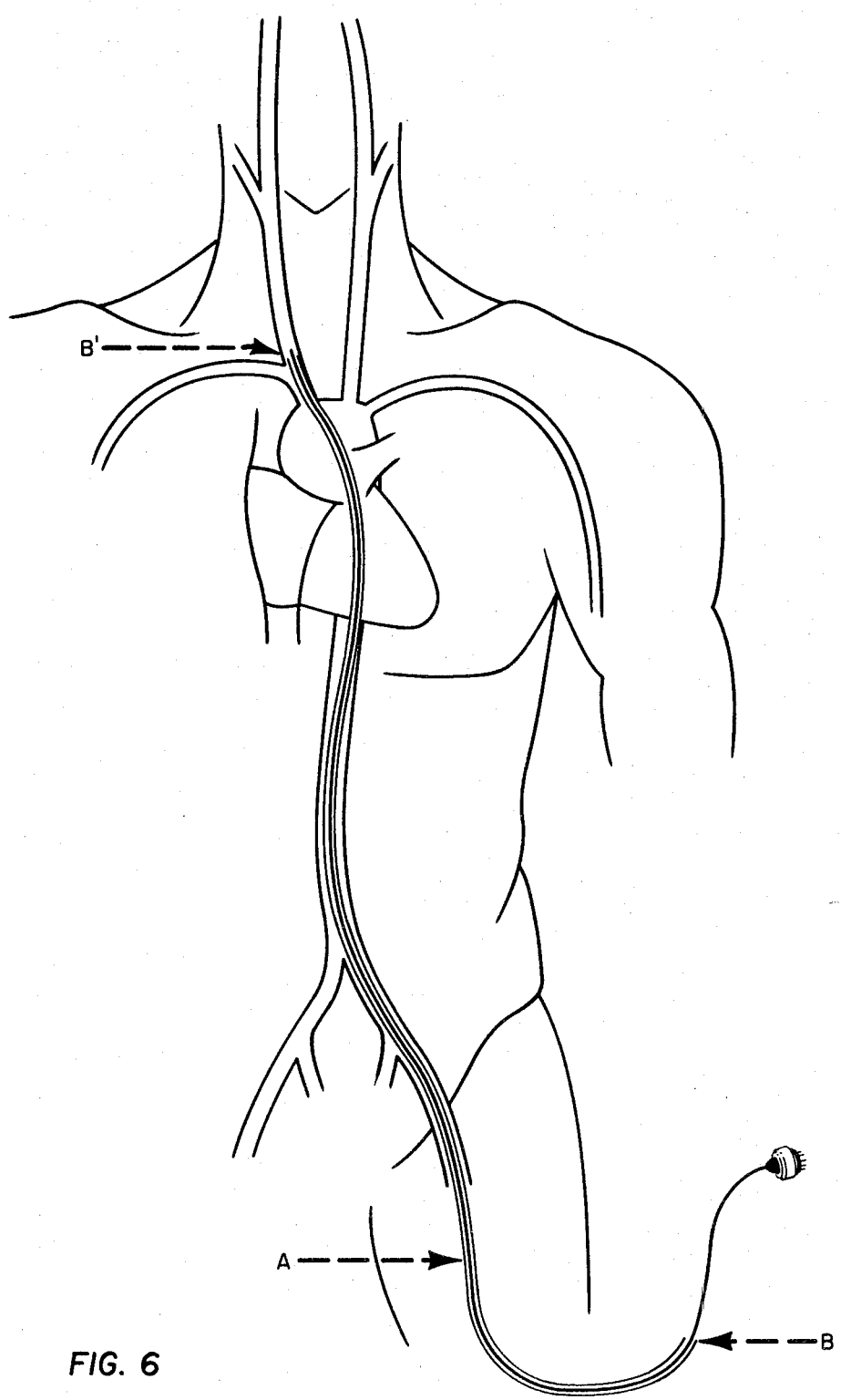
FIG. 6 shows the catheter in place with the larger catheter withdrawn.

Referring to FIG. 1, one method of introducing catheter 11 into living organism 9 is directly through an internal carotid puncture 8, continuously with a needle and plastic canula (like the intracath needle and canula). When this route of insertion is followed the measurements should be done quickly and the catheter and plastic canula withdrawn. To prevent leakage of blood, a rubber stopper is used at the outer end of the canula through which the puncture needle is replaced by the internal carotid catheter. Internal Carotid Catheters may also be inserted through one of the femoral arteries against the blood stream and inside a larger catheter until it reaches the internal carotid artery (FIG. 5). The larger catheter is then withdrawn (FIG. 6) for 12 cms and the measurements are performed. The internal carotid catheter is not covered by the larger catheter which should then only serve to guide the carotid catheter and keep it in position against the blood stream.

The size and the resistance of heating coil 12 and platinum resistance thermometer 15 are determined in part by the size of the catheter. For the present invention, the length of heating coil 12 varies from 4–5 centimeters (2½ centimeters for pediatrics) and the range of the length of resistance thermometer 15 is 3 to 4 centimeters (2 centimeters for pediatrics). The windings on the catheter are made with a weaving machine as is known in the art. The size of heating coil 12 and resistance thermometer 15 also depends on which accessible arteries are to be studied.

The surface area to volume flow ratio must be considered. For example, in the present invention for study of blood flow in the carotid artery, the flow is about 300 milliliters per minute while cardiac output ranges between 4000 and 12,000 milliliters per minute. using the equation for the area of a cylinder, $2\pi rh$, where, $\pi$ equals $3.14.6\ldots$, r is the radius of the catheter body 11 in mm, and h is the length of the windings in mm, and the above given lengths for heating coil 12 and resistance thermometer 15 along with an outside diameter of 0.8 mm for heating coil winding 12 and 14 mm for resistance thermometer winding 15, the surface area to volume flow ratios may be computed. In the present embodiment they are .21-.42 mm$^2$/ml/min for heating coil 12 and 0.08-0.17 mm$^2$/ml/min for resistance thermometer 15.

If the same ratio in the design of the present invention were utilized on the cardiac catheter the heating coil would be 100 centimeters long and the platinum resistance thermometer would be 50 centimeters long. These lengths would be unacceptable for the cardiac catheter.

The reason that the cardiac catheter requires relatively shorter heating and thermometer coils is that the stable base line obtained by it depends on the mixing produced by: (1) the pumping action of the right ventricle; (2) the turbulent flow distal to the pulmonary valve; (3) the continuous movement of the catheter in the right ventricle and pulmonary artery with each heart beat. Also, the present invention requires a lower rate of heating than the right cardiac catheter because of the temperature stability in the arterial system as compared with the venous system with its respiratory fluctuations.

The overall length of the catheter should be selected according to (1) the site from which it is introduced to reach the regional blood flow to be measured, and (2) size of the patient or experimental animal. The length of heating coil 12, resistance thermometer 15 and distance between them depends on the expected range of the minute volume of blood flow at the site. Thus, catheters of several sizes and lengths, each for its own expected range of blood flow measurement may be needed.

Referring to FIG. 2, the heat applied by heating coil 12 at a predetermined constant rate need not exceed 6 seconds in duration inasmuch as the temperature rise, recorded by downstream platinum resistance thermometer 15, reaches the plateau by an asymptote within four seconds due to the high blood velocity in the artery. This relatively short heating time reduces the recirculation problem which has affected prior devices and methods. In addition, the capillary bed acts as a very large heat "sink" which also minimizes recirculation problems. The modest mean temperature rise ranges between 0.04° C. and 0.15° C. This rise affects only the volume flow during the period of heating and not the entire minute volume and is therefore not likely to affect heart function or blood vessel intima during or after the measurements.

If the internal carotid catheter is introduced through the neck, a second electrode should be attached directly on the subject in addition to electrode 12 at the tip of catheter 11. On the other hand if the carotid catheter is introduced through the femoral artery the second electrode may be placed on catheter 11 in a position so as to be located before the heart. Both these electrodes are optional because it may be easier to obtain electrographic tracings with conventional electrodes on the subject.

Referring to FIG. 4, distal platinum resistance thermometer 15 is connected with a three lead thermometer bridge. This is because lead wires 16 pass directly under proximal heating coil 19. Although they are separated by inert and insulating plastic coating 27 (see FIG. 3) and the resistance of copper lead wires 16 is minimal, when heat is applied to heating coil 19 there is direct heat conduction from heating coil 19 to underlying lead wires 16. This causes an increase in the resistance of lead wires 16 which would produce an imbalance that may be even greater than the expected deflection in the same or in the opposite direction. Therefore, because of the three lead bridge, the degree of deflection is not affected by heat conducted to the lead wires and is directly proportional to the rate of heating applied and inversely proportional to volume flow.

The three lead thermometer bridge is energized by lead wire 16g which is connected to voltage source 28. Lead wire 16e along with platinum resistance thermometer 15 form the upper right arm of the bridge. Lead wire 16f along with variable resistor 29A form the upper left arm of the bridge. Lead wires 16e and f are identical and are taken from the same reel, and wound adjacent to each other and extend under heating coil 19 for the same distance. When heat is applied the change in the resistance of lead wires 16e and f is the same and no misleading imbalance is detected by galvanometer 29.

In the present invention automatic suppression and D.C. recorder 31 for balancing the bridge is provided in the design of the electronic apparatus necessary to obtain thermodilution measurements. A predetermined rate of heating can be introduced only after automatic balancing of the bridge is reached. During the balancing time, a push button on the face of direct readout recorder 36 is lit with a sign to "wait" when automatic balancing of the bridge is reached, the "wait" light is turned off and another push button with a sign "exp." (exposure) is lit indicating that the electronic circuit is ready to introduce heat. When "exp." button is pushed, the predetermined rate of heating starts and remains on for the predetermined number of seconds and automatic suppression and D.C. recorder 31 is disconnected. On starting "exposure" and throughout the exposure time, the automatic balancing device is cancelled so that the required deflection is obtained. The automatic balancing of the bridge is reactivated after the heating time is over.

Referring to FIG. 2, resistance thermometer 15 is made of 99.99% pure platinum wires 0.02-0.3 millimeters O.D. Heating coil 19 is made of constantan wires 0.04 millimeters O.D. All of the wires in heating coil 19 and resistance thermometer 15 are electrically insulated with a double polyurethane coating which melts during the soldering process. These fine wires cannot stand even extra fine sandpaper to remove the conventional enamel insulation.

Platinum wires were used for thermometer winding 15 in order to obtain a high resistance. Copper may also be used in a resistance thermometer but the resistance is too low for short windings. Platinum has a high strain coefficient of resistivity but strain errors can be eliminated. Two types of errors are caused by strain phenomena in a thermometer material. The first is strain caused by winding and coating of the thermometer while making the catheter. This source of error is corrected by measuring the new temperature coefficient of the resistance thermometer, that is, finding the resistance of the thermometer at 0° C. and at 100° C.

The second type of strain error is caused by rhythmic movements of thermometer with heart beats and the change of O.D. of the catheter caused by changing pressures of systole and diastole during the measuring time. These rhythmic movements of the catheter and changes in its O.D. affect the strain coefficient of resistivity of the wound thermometer. At rest these movements are repetitive and cause almost identical waves which may be filtered. However, during exercise the body movements and deep respiratory movements are reflected on the base line with irregular waves and affect the accuracy of each measurement. Use of a double spiral thermometer winding overcomes this problem.

The resistance (and impedance) of heating coil 19 is also kept at a predetermined level by reducing or increasing the number and length of the wires used in parallel, to suit the range of blood to be measured. An impedance of 50 ohms was chosen for use with the present invention. This impedance was selected for use with the present invention because high frequency power and coaxial cables were employed with the invention. The reason for the bifilar winding of heating coil 19 is to cancel inductance between the wires of the coil while applying high frequency alternating current.

The volume of blood flow, which is directly proportional to the rate of heating and inversely proportional to temperature rise is obtained from the following formula:

$$\text{Volume Flow} = \frac{W \times 0.239 \times 60}{0.92 \times T}$$

Where:
W is the predetermined rate of high frequency power in Watts, which is supplied to heater 12,
0.239 is the conversion factor from watts to calories,
60 is the conversion factor to obtain the minute volume,
0.92 is the product of specific heat (0.87) and density (1.056) of the blood,
T is the rise of the mean temperature of blood flowing through the carotid artery. An electrical standardization equal to a temperature rise of 0.1° C. is recorded before each measurement by inducing an imbalance in the bridge by means of a push button that connects a resistor in parallel with one of the lower arms of the bridge. The value of this resistor and the resulting imbalance is calculated to be equal to 0.1° C.

An advantage in having a constant predetermined heating coil resistance is that it allows for a direct milliliter per minute reading in direct readout recorder 36. This is accomplished by taking the above blood flow equation and substituting ($V^2/R$) for W where V is the voltage applied to the heater and R is the heating coil resistance. Because R is now 50 ohms the equation simplifies to:

Blood flow ml/min. = ($V^2/T$) × 0.311

Where:
V is the voltage applied to heater; and
T is the rise in mean temperature of blood flowing through the artery. Since the applied voltage and temperature rise are readily available, the blood flow can be directly computed inside the apparatus and a direct readout in milliliters per minute is made available. This is done by including analog multipliers inside direct readout recorder 36 to square the applied voltage divided by the observed temperature rise, and multiply by the 0.311 constant. Direct readout provides a significant advantage over prior devices in that it makes data available more quickly and avoids computation errors.

Continual measurements of blood flow within a few seconds using this invention offers a number of other advantages. For example, each measurement can be carried out without the injection of any substance into the blood stream. Other thermodilution measurements made in man and in experimental animals have utilized a saline injection during each measurement. These injections are likely to increase cardiac output during the measuring period, and the error is further enlarged when the minute volume is calculated. Furthermore the flexible connections to the subject allow the application of heat and measurements of temperature rise with ease and without sacrifice of accuracy. The invention also makes it possible to apply heat and obtain the signal indicative of temperature rise by telemetry.

Many modifications and applications of the present invention are possible in the light of the above teaching. For example, when the invention is introduced into the internal carotid artery either directly or via the femoral artery, repeated measures of the internal carotid blood flow during intensive care and surgery may be made. The internal carotid blood flow measurements can be used to prove the first sign of death in intensive care units since at the time of death cerebral circulation stops, even when the heart is still beating as the patient is kept "alive" with a respirator and a pacemaker.

In light of the foregoing it is therefore understood that within the scope of the disclosed inventive concept, the invention may be practiced otherwise than specifically described.

What is claimed is:

1. In a bioelectric measuring apparatus for insertion within an internal carotid artery of a living organism, including in combination, an elongated, flexible body, an electrical heater mounted thereon, and a temperature sensing device also mounted on said catheter body, the improvement comprising:
   temperature transducing means mounted on said catheter body for sensing the temperature rise of said catheter body produced by said electrical heater; and
   wherein said temperature sensing device and said electrical heater include wire windings having dimensions to facilitate compact placement within said organism and to achieve a predetermined surface area to blood volume flow ratio of from about 0.08 mm$^2$/ml/min. to about 0.42 mm$^2$/ml/min.

2. An improved bioelectric measuring apparatus for insertion within a living organism according to claim 1 wherein said electrical heater wire is bifilarly wound.

3. An improved bioelectric measuring apparatus for insertion within a living organism according to claim 1 further comprising:
   conducting means, mounted on said catheter body, for electrical contact with said living organism.

4. An improved bioelectric measuring apparatus for insertion within a living organism according to claim 3 wherein said conducting means comprises one or more electrodes.

5. An improved bioelectric measuring apparatus for insertion within a living organism according to claim 4 wherein said electrodes comprise bare platinum wire electrodes.

6. An improved bioelectric measuring apparatus for insertion within a living organism according to claim 1 wherein said temperature transducing means comprises;
   a first thermocouple positioned on said catheter body along said electrical heater wire winding;

a reference thermocouple positioned on said catheter body in series with said first thermocouple and proximal to said electric heater wire winding.

7. An improved bioelectric measuring apparatus for insertion within a living organism according to claim 6 wherein said thermocouples are copper constantan thermocouples.

8. An improved bioelectric measuring apparatus for insertion within a living organism according to claim 1 wherein said temperature sensing wire winding comprises 99.99% pure platinum wires.

* * * * *